(12) United States Patent
Sasaki et al.

(10) Patent No.: US 12,239,556 B2
(45) Date of Patent: Mar. 4, 2025

(54) STENT

(71) Applicant: OLYMPUS CORPORATION, Tokyo (JP)

(72) Inventors: Kanta Sasaki, Hachioji (JP); Ryoji Hyuga, Kamiina-gun (JP); Kosuke Ozawa, Hachioji (JP); Hirofumi Taniguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 767 days.

(21) Appl. No.: 17/480,431

(22) Filed: Sep. 21, 2021

(65) Prior Publication Data
US 2022/0000643 A1 Jan. 6, 2022

Related U.S. Application Data

(63) Continuation of application No. PCT/JP2019/012860, filed on Mar. 26, 2019.

(51) Int. Cl.
*A61F 2/915* (2013.01)
*A61F 2/95* (2013.01)

(52) U.S. Cl.
CPC .............. *A61F 2/915* (2013.01); *A61F 2/95* (2013.01); *A61F 2002/9155* (2013.01); *A61F 2210/0014* (2013.01); *A61F 2240/001* (2013.01)

(58) Field of Classification Search
CPC .............. A61F 2/915; A61F 2/848; A61F 2002/91558; A61F 2/86
See application file for complete search history.

(56) References Cited

U.S. PATENT DOCUMENTS

| | | | |
|---|---|---|---|
| 9,622,888 B2 * | 4/2017 | Armstrong | A61F 2/89 |
| 2005/0131515 A1 * | 6/2005 | Cully | A61F 2/07 623/1.13 |
| 2011/0071618 A1 * | 3/2011 | Baldwin | B21F 45/008 29/428 |
| 2013/0073029 A1 * | 3/2013 | Shaw | A61B 17/12172 623/1.36 |
| 2013/0138202 A1 * | 5/2013 | Paul | A61F 2/915 623/1.15 |

(Continued)

FOREIGN PATENT DOCUMENTS

| | | |
|---|---|---|
| JP | 4451421 B2 | 4/2010 |
| JP | 2015-510429 A | 4/2015 |
| JP | 5876019 B2 | 3/2016 |

(Continued)

OTHER PUBLICATIONS

International Search Report dated Jun. 11, 2019 received in PCT/JP2019/012860.

*Primary Examiner* — Sarah W Aleman
(74) *Attorney, Agent, or Firm* — Scully, Scott, Murphy & Presser, P.C.

(57) ABSTRACT

The stent having self-expandability, the stent including: a body part formed in a tubular shape by a wire; and a first locking part and a second locking part protruding outward in a radial direction of the body part and formed by the wire. A first angle formed by a protrusion direction of the first locking part and an axial direction of the body part is different from a second angle formed by a protrusion direction of the second locking part and the axial direction.

20 Claims, 9 Drawing Sheets

(56) References Cited

U.S. PATENT DOCUMENTS

2015/0025618 A1 1/2015 Kim
2016/0106559 A1 4/2016 Shin et al.

FOREIGN PATENT DOCUMENTS

| JP | 2016-077884 A | 5/2016 |
|----|---------------|--------|
| KR | 10-2011-0062355 A | 6/2011 |
| KR | 10-2017-0094918 A | 8/2017 |

* cited by examiner

STENT

The present invention relates to a stent that expands a tubular portion. This application is a continuation application based on International Patent Application No. PCT/JP2019/012860 filed on Mar. 26, 2019, and the content of the PCT international application is incorporated herein by reference.

BACKGROUND

In recent years, a stent indwelling technique has been used to expand and hold a lumen of a tubular organ by indwelling a stent made of a wire rod (wire) or the like in an affected area in which stenosis or occlusion occurs in a lumen of the tubular organ in a living body.

The stent having self-expandability (self-expandable stent) is transported in a reduced diameter state to the affected area in which stenosis or occlusion occurs by a delivery system. The stent released from the delivery system expands in diameter by the self-expandability to expand stenosis or occlusion.

In many cases, the lumen in which such a stent is indwelled is bent, and thus the stent is required to have a function of maintaining a shape corresponding to a shape of the bent lumen (lumen shape maintenance function). The stent is required to have a function of stably maintaining an indwelled position (indwelled position maintenance function).

The stent disclosed in Japanese Patent No. 5876019 includes a tubular body part and a locking part. The locking part protrudes in a direction away from an outer circumference of the tubular body part. In the stent disclosed in Japanese Patent No. 5876019, in a case in which the stent is inserted into the lumen, the position of the stent can be stably maintained in the lumen by the elasticity of the locking part.

SUMMARY

A stent according to the disclosure is a stent having self-expandability, the stent including: a body part formed in a tubular shape by a wire; and a first locking part and a second locking part protruding outward in a radial direction of the body part and formed by the wire. A first angle formed by a protrusion direction of the first locking part and an axial direction of the body part is different from a second angle formed by a protrusion direction of the second locking part and the axial direction.

A method according to the disclosure, the method for indwelling a stent into a tubular organ, the stent including a body part formed in a tubular shape, first and second locking parts protruding outward in a radial direction of the body part, the method including steps of: accommodating the stent being in a reduced diameter state into a delivery system; delivering the stent to an indwelling target position by the delivery system; indwelling the stent while expanding a diameter of the stent into the tubular organ by the delivery system such that the first angle formed by a protrusion direction of the first locking part and an axial direction of the body part is different from a second angle formed by a protrusion direction of the second locking part and the axial direction.

DETAILED DESCRIPTION OF EXEMPLARY EMBODIMENTS

A stent according to an embodiment will be described with reference to FIGS. 1 to 6.

Figure 1:
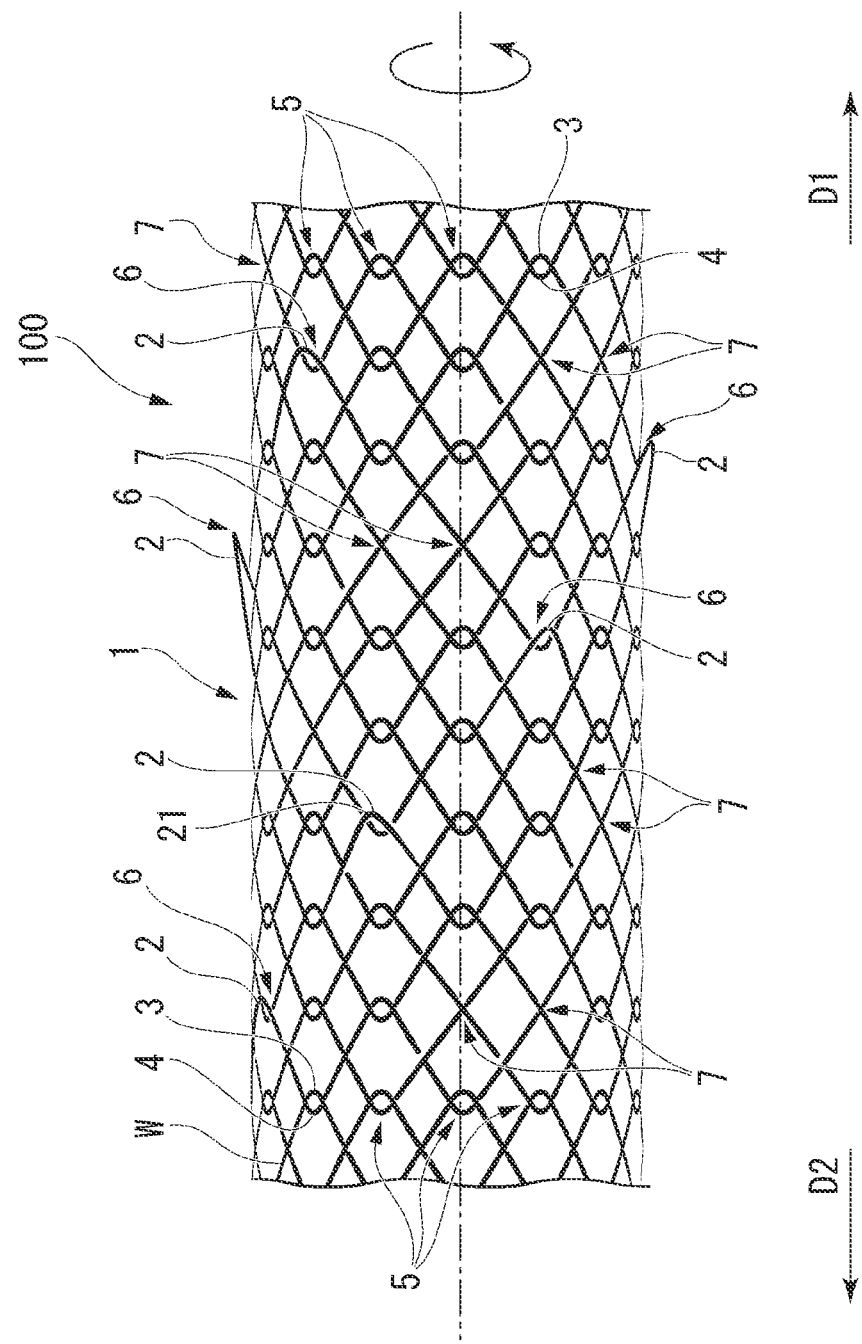
FIG. 1 is a view showing the overall configuration of a stent according to an embodiment.
Figure 2:
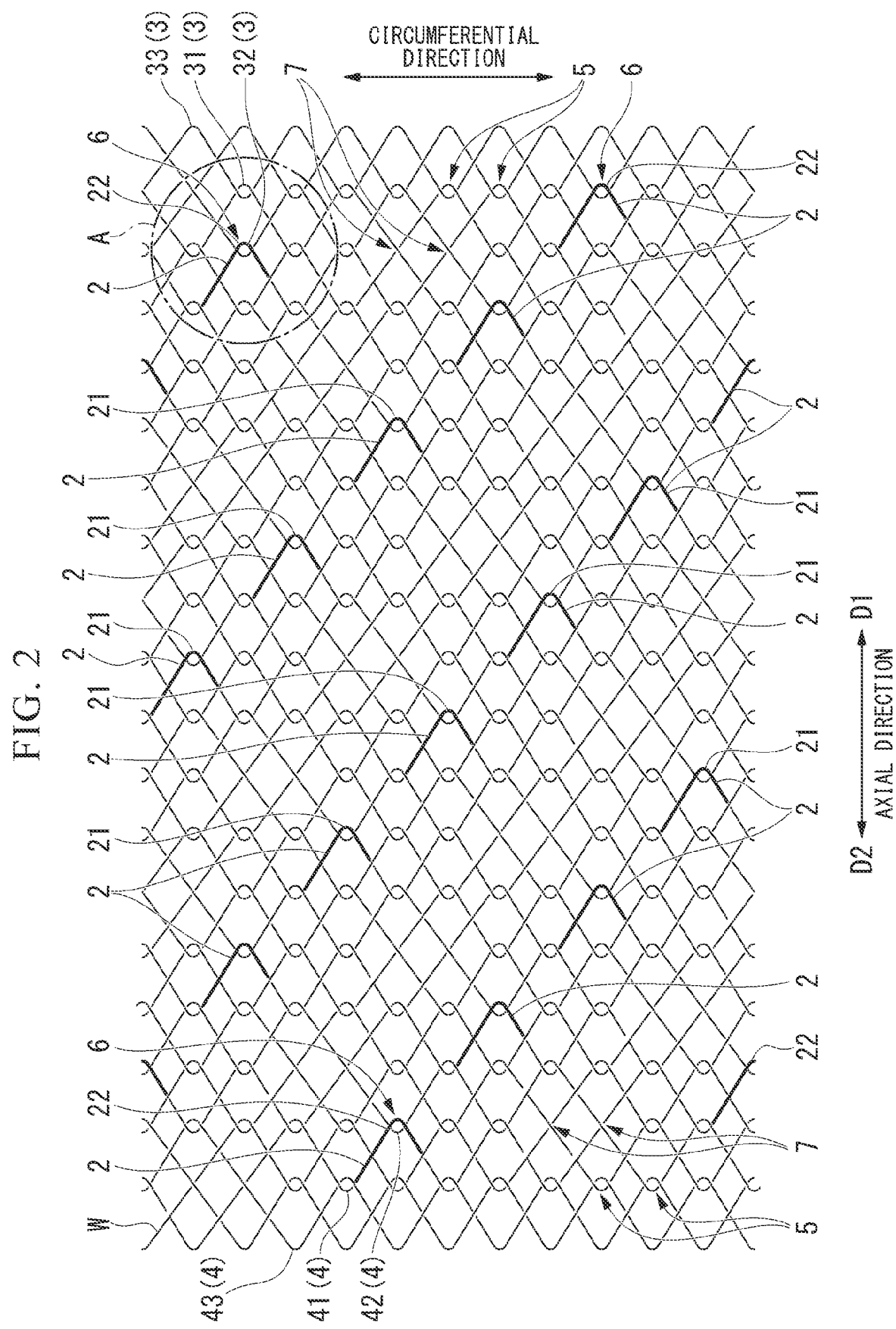
FIG. 2 is a developed view of the stent, which is developed in a circumferential direction.

FIG. 1 is a view showing an overall configuration of a stent 100 according to the present embodiment. FIG. 1 shows the overall configuration of the stent 100 in a state of being self-expanded. FIG. 2 is a developed view of the stent 100, which is developed in a circumferential direction.

The stent 100 is formed by weaving a wire W, and has a tubular shape. The stent 100 has self-expandability. The stent 100 is placed in a body lumen of a digestive system such as a bile duct, an esophagus, a duodenum, a small intestine, and a large intestine, and is mainly used for the purpose of expanding and holding the lumen. The stent 100 according to the present embodiment is not a so-called covered stent in which an outer circumferential surface side thereof is coated with a resin film or the like, but is an uncovered stent, which is not coated with the film or the like. Here, the stent 100 can also be used as the covered stent by being coated with the resin film or the like.

As shown in FIG. 1, the stent 100 includes a body part 1 and locking parts 2. The body part 1 is formed into the tubular shape by the wire W. The locking parts 2 are formed by the wire W. In the following description, one side in an axial direction of the stent 100, which is a distal side, is also referred to as a "first axial direction D1", and the other side in the axial direction of the stent 100, which is a proximal side, is also referred to as a "second axial direction D2".

As shown in FIGS. 1 and 2, the stent 100 includes a bent-crossing portion 5, a non-entangled portion 6, and a straight crossing portion 7. The wires W are bent and cross each other to form the bent-crossing portion 5. The wires W are bent to form the non-entangled portion 6. The wires W cross each other in a straight line to form the straight crossing portion 7.

Figure 3:
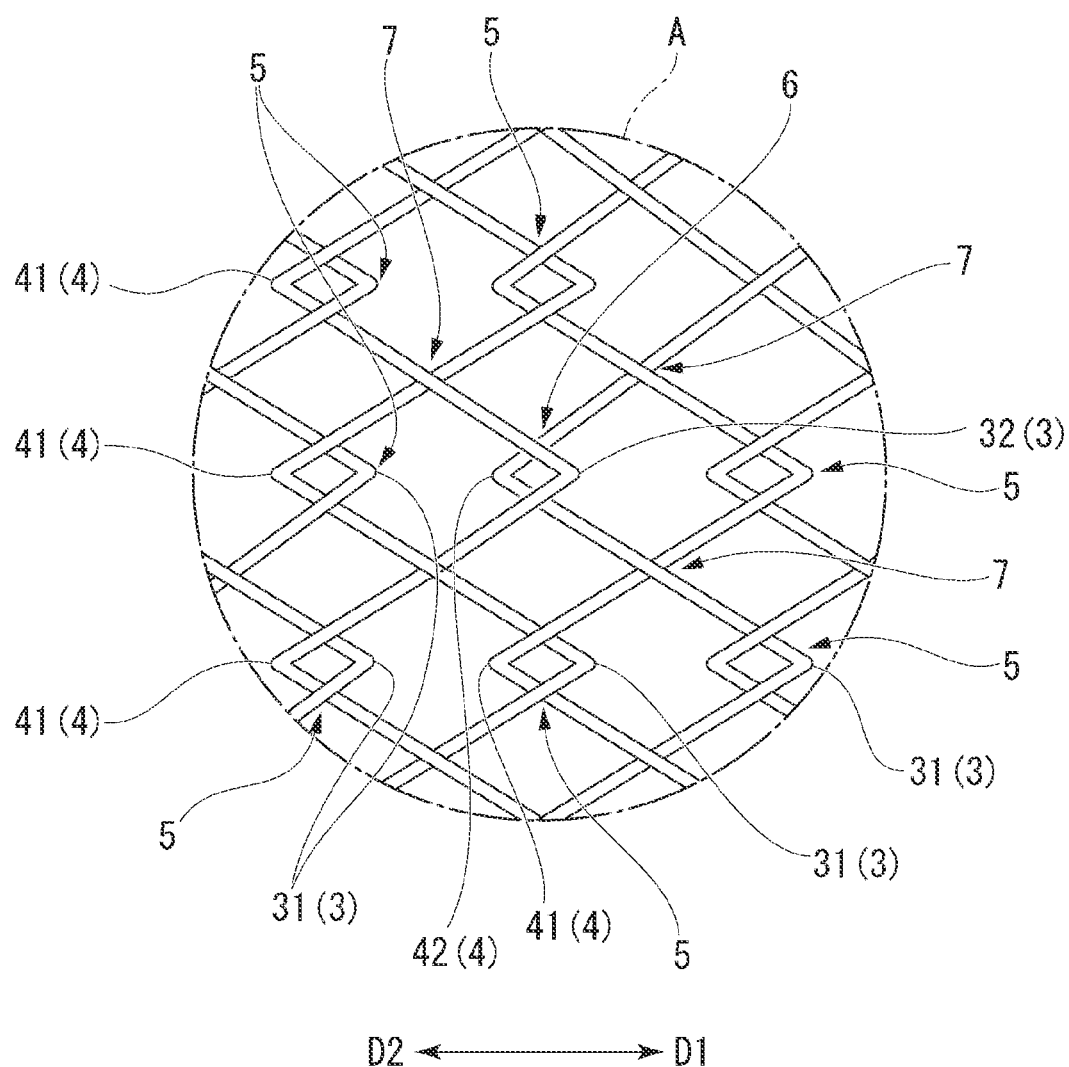
FIG. 3 is an enlarged view of a portion indicated by a dashed line in FIG. 2.

FIG. 3 is an enlarged view of a portion indicated by a dashed line in FIG. 2.

The wire W forms a first bent portion 3 and a second bent portion 4. The first bent portion 3 is bent to be a convex toward the side of the distal end (a side of a first axial direction D1), which is one end side of the stent 100. The second bent portion 4 is bent to be a convex toward the side of the proximal end (a side of a second axial direction D2), which is the other end side of the stent 100. The first bent portion 3 and the second bent portion 4 are alternately formed along the wire W.

As shown in FIG. 3, the bent-crossing portion 5 is formed by crossing a first part 31 of the first bent portion 3 and a first part 41 of the second bent portion 4 with each other in a radial direction. At the bent-crossing portion 5, the first part 31 of the first bent portion 3 and the first part 41 of the second bent portion 4 cross each other and are entangled in a "hook shape", so that the first part 31 of the first bent portion 3 and the first part 41 of the second bent portion 4 are inseparably connected so as to be relatively movable.

As shown in FIG. 3, the non-entangled portion 6 is formed by a second part 32 of the first bent portion 3 (a part of the first bent portion 3 that does not form the bent-crossing portion 5) and the second part 42 of the second bent portion 4 (a part of the second bent portion 4 that does not form the bent-crossing portion 5), and the second part 32 of the first bent portion 3 is disposed outside the second part 42 of the second bent portion 4 in the radial direction. At the non-entangled portion 6, the second part 32 of the first bent portion 3 and the second part 42 of the second bent portion 4 do not cross each other in the radial direction and are not entangled.

As shown in FIGS. 2 and 3, the non-entangled portion 6 is formed at a position interposed between the bent-crossing portions 5 along the wire W. Specifically, as shown in FIG. 3, the second part 32 of the first bent portion 3 that forms the non-entangled portion 6 is interposed between two first parts 41 of the second bent portions 4 along the wire W. The lengths of the wire W from the second part 32 of the first bent portion 3 to two first parts 41 of the second bent portions 4 that interpose the second part 32 of the first bent portion 3 are equal. The second part 42 of the second bent portion 4 that forms the non-entangled portion 6 is interposed between two first parts 31 of the first bent portions 3. The lengths of the wire W from the second part 42 of the second bent portion 4 to two first parts 31 of the first bent portions 3 that interpose the second part 42 of the second bent portion 4 are equal.

In the stent 100, as shown in FIG. 2, rows of the straight crossing portions 7 arranged in the circumferential direction are arranged at equal intervals in the axial direction. Between the rows of the straight crossing portions 7 arranged in the circumferential direction, the bent-crossing portion 5, the non-entangled portion 6, and the straight crossing portion 7 are arranged in the circumferential direction. Among the bent-crossing portion 5, the non-entangled portion 6, and the straight crossing portion 7 arranged in the circumferential direction, only one non-entangled portion 6 is formed.

As shown in FIG. 2, a remaining portion 33 of the first bent portion 3 or a remaining portion 43 of the second bent portion 4, which does not form the bent-crossing portion 5 or the non-entangled portion 6, forms an end part of the stent 100. The remaining portion 33 of the first bent portion 3 or the remaining portion 43 of the second bent portion 4, which does not form the bent-crossing portion 5 or the non-entangled portion 6, may be formed at a place other than the end part of the stent 100.

The locking part 2 is formed by the wire W, and is the second part 32 of the first bent portion 3 that forms the non-entangled portion 6. As shown in FIG. 1, a tip end of the first bent portion 3 of the locking part 2 protrudes to the outermost side in the radial direction. The locking parts 2 are uniformly provided in the stent 100 over the axial direction.

The body part 1 is a hollow tubular member formed by the wire W. The body part 1 is formed by the wire W excluding the locking part 2. That is, the body part 1 is formed by the bent-crossing portion 5, the second part 42 of the second bent portion 4 of the non-entangled portion 6, and the straight crossing portion 7. Since the first part 31 of the first bent portion 3 and the first part 41 of the second bent portion 4 are connected so as to be relatively movable at the bent-crossing portion 5, the body part 1 is capable of being curved or expanded and contracted as a whole.

A region surrounded by four intersections selected from the bent-crossing portion 5, the non-entangled portion 6, and the straight crossing portion 7, and not including the bent-crossing portion 5, the non-entangled portion 6, and the straight crossing portion 7 inside the region is defined as a "cell". As shown in FIG. 1, the locking part 2 does not protrude beyond the region of the cell in the axial direction. Therefore, the locking part 2 does not overlap with the bent-crossing portion 5 or the straight crossing portion 7 in the axial direction.

Figure 4:
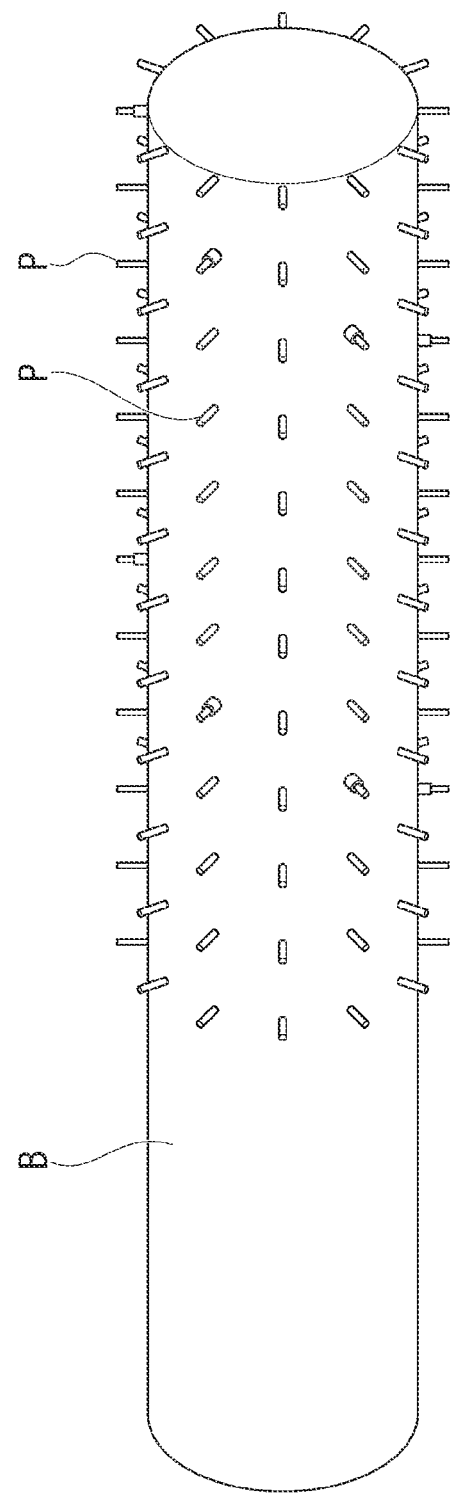
FIG. 4 is a view showing a manufacturing jig of the stent.

FIG. 4 is a view showing a manufacturing jig J of the stent 100.

The manufacturing jig J is formed by a cylindrical main body B and a plurality of pins P erected on an outer circumferential surface of the main body B. The wire W is hooked on the pin P to manufacture the tubular stent 100. The pin P includes a pin P1 for manufacturing the bent-crossing portion 5 and a pin P2 for manufacturing the non-entangled portion 6.

The wire W is made of a super-elastic alloy containing NiTi as a main material. The super-elastic alloy containing NiTi as the main material is not permanently deformed at the time of weaving, and a woven shape thereof is stored by performing heat treatment in a woven state.

Figure 5:
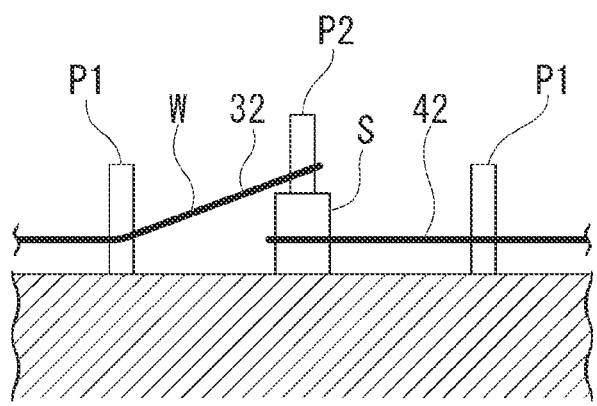
FIG. 5 is a view showing a pin for manufacturing a non-entangled portion among the pins of the manufacturing jig.

FIG. 5 is a view showing the pin P2 of the manufacturing jig J.

The pin P2 includes a spacer S having a diameter dimension larger than that of another portion in the vicinity of a connection portion with the main body B. In the manufacture of the non-entangled portion 6, the second part 32 of the first bent portion 3 is hooked on a step formed at a tip end part of the spacer S of the pin P2. The second part 42 of the second bent portion 4 is hooked on a side portion of the spacer of the pin P2. By using the pin P2 of the manufacturing jig J, the second part 32 of the first bent portion 3 is disposed outside the second part 42 of the second bent portion 4 in the radial direction, and the non-entangled portion 6 is easily manufactured. On the other hand, as shown in FIG. 5, the pin P1 does not include the spacer S.

The non-entangled portion 6 is manufactured by the pin P2 of the manufacturing jig J, and an angle formed by a protrusion direction of the locking part 2 and the axial direction of the body part 1 is an acute angle.

Hereinafter, an operation of the stent 100 will be described.

The stent 100 is accommodated in a delivery system in a reduced diameter state and transported to an affected area in which stenosis or occlusion occurs. Unlike the stent disclosed in Japanese Patent No. 5876019, the stent 100 does not have a structure in which the locking part is separately provided and has a simple configuration. Therefore, a storage diameter of the stent 100 in a case of being accommodated in the delivery system is capable of being reduced.

That is, the locking part 2 does not hinder the storage of the stent 100 in the delivery system.

Specifically, in the stent 100, occupied volumes of the wire W per unit volume in a portion in which the locking part 2 is formed and in a portion in which the locking part 2 is not formed are equal. Therefore, the stent 100 can be uniformly reduced in diameter as a whole, and the stent 100 is easily accommodated in the delivery system. Therefore, the ease of reducing the diameter of the stent 100 is the same as the ease of reducing the diameter of a general stent formed by the bent-crossing portion 5 including no locking part 2 and the straight crossing portion 7.

The stent 100 released from the delivery system expands in diameter due to the self-expandability to expand stenosis or occlusion. A tip end of the locking part 2, that is, a tip end of the second part 32 of the first bent portion 3, all faces the first axial direction D1. Therefore, the removability of the stent 100 is the same as the removability of a general stent which includes the straight crossing portion 7 and the bent-crossing portion 5 and not includes locking part 2.

Figure 6:
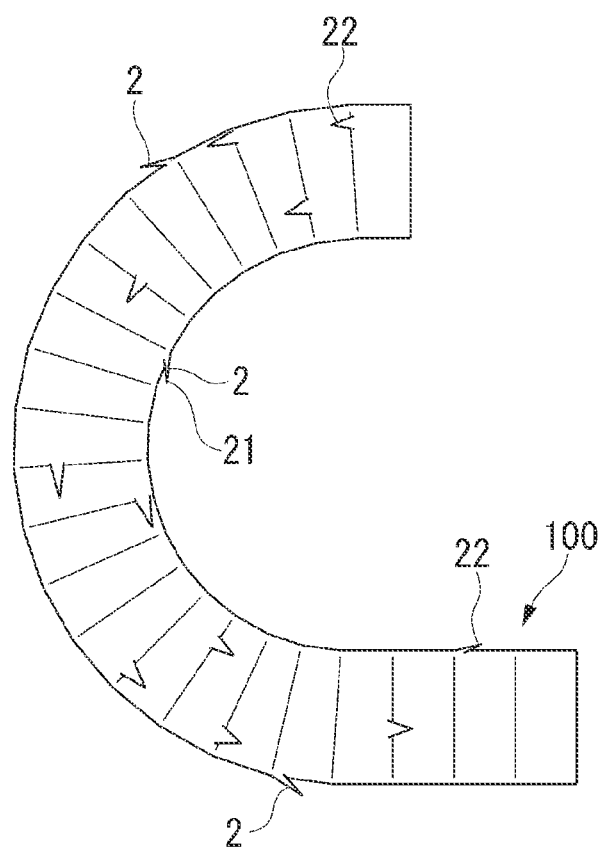
FIG. 6 is a view showing the bent stent.

FIG. 6 is a view showing the bent stent 100.

Since the first part 31 of the first bent portion 3 and the first part 41 of the second bent portion 4 are connected so as to be relatively movable at the bent-crossing portion 5, the stent 100 is capable of being bent as a whole.

In the stent 100, in a case in which the entire stent 100 is bent with respect to a longitudinal axis as shown in FIG. 6, the first part 31 of the first bent portion 3 and the first part 41 of the second bent portion 4 are relatively moved and bent without "elastic deformation" of the wire which is a super-elastic alloy. As a result, the stent 100 can maintain a bent shape without returning to its original shape. That is, the stent 100 has a function of maintaining a shape corresponding to the shape of the bent lumen (pipeline shape maintenance function).

As shown in FIG. 6, the tip end of the locking part 2, that is, the tip end of the second part 32 of the first bent portion 3 is hooked on the stenosis or occlusion, so that the stent 100 has a function of stably maintaining an indwelling position (indwelling position maintenance function).

Since the tip end of the locking part 2, that is, the tip end of the second part 32 of the first bent portion 3 all faces the first axial direction D1, the stent 100 is difficult to be moved toward the distal direction (the side of the first axial direction D1) and is easily moved toward the proximal direction (the side of the second axial direction D2). Therefore, the stent 100 has a function of preventing the stent 100 from straying into the distal side of the tubular organ (the side of the first axial direction D1) (stray prevention function).

As shown in FIG. 6, the stent 100 is bent around a portion in which the bent-crossing portions 5 are arranged in the circumferential direction. Since the bent-crossing portion 5 and the non-entangled portion 6 are arranged in the circumferential direction, the tip end of the locking part 2 of the bent stent 100 easily protrudes outward in the radial direction as shown in FIG. 6. Therefore, the stent 100 is capable of more suitably exerting the indwelling position maintenance function when the stent 100 is bent.

In the stent 100, the tip end of the locking part 2, that is, the tip end of the second part 32 of the first bent portion 3, faces the first axial direction D1, and thus the stent 100 can be easily re-stored (recaptured) in the delivery system positioned on the side of the second axial direction D2. That is, the stent 100 does not impair a recapture function capable of being easily re-stored (recaptured) in the delivery system.

With the stent 100 according to the present embodiment, the function of stably maintaining the indwelling position (indwelling position maintenance function) is provided, in which the operation of storing the stent in the delivery system, the operation of removing the stent, the operation of recapturing the stent, or the like is easily performed.

While preferred embodiments of the stent have been described and illustrated above, it should be understood that these are exemplary of the stent and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims. Also, a configuration can be adopted in which the constituent elements shown in the embodiment described above and the modified examples are appropriately combined.

Modified Example 1

For example, in the embodiment described above, the tip end of the locking part 2, that is, the tip end of the second part 32 of the first bent portion 3, is bent toward the side of the first axial direction D1 to be a convex as shown in FIG. 3, but an aspect of the tip end of the locking part is not limited thereto.

Figure 7:
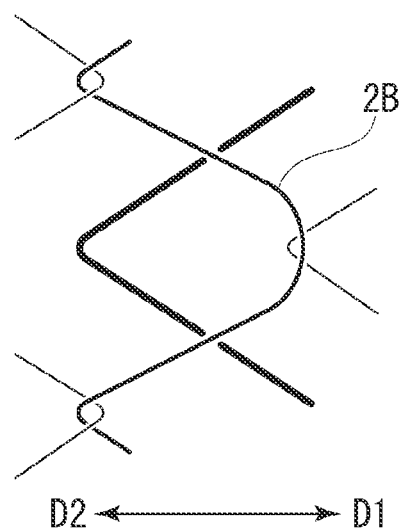
FIG. 7 is a view showing a modified example of a locking part of the stent.

FIG. 7 is a view showing a locking part 2B, which is a modified example of the locking part. A tip end of the locking part 2B is gently bent toward the side of the first axial direction D1 to be a convex.

Figure 8:
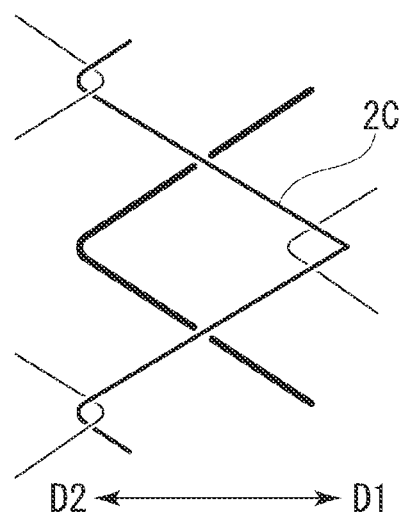
FIG. 8 is a view showing a modified example of the locking part of the stent.

FIG. 8 is a view showing a locking part 2C, which is a modified example of the locking part. A tip end of the locking part 2C is sharply bent toward the side of the first axial direction D1 to be a convex.

Figure 9:
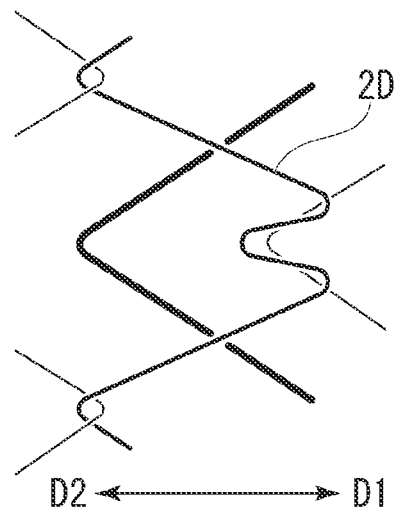
FIG. 9 is a view showing a modified example of the locking part of the stent.

FIG. 9 is a view showing a locking part 2D, which is a modified example of the locking part. A tip end of the locking part 2D is bent a plurality of times to be a convex toward the side of the first axial direction D1.

The locking part 2B, the locking part 2C, and the locking part 2D exert the indwelling position maintenance function and the like as in the locking part 2.

Modified Example 2

For example, in the embodiment described above, the locking parts 2 are uniformly provided in the stent 100 in the axial direction, but an aspect of the stent is not limited thereto.

Figure 10:
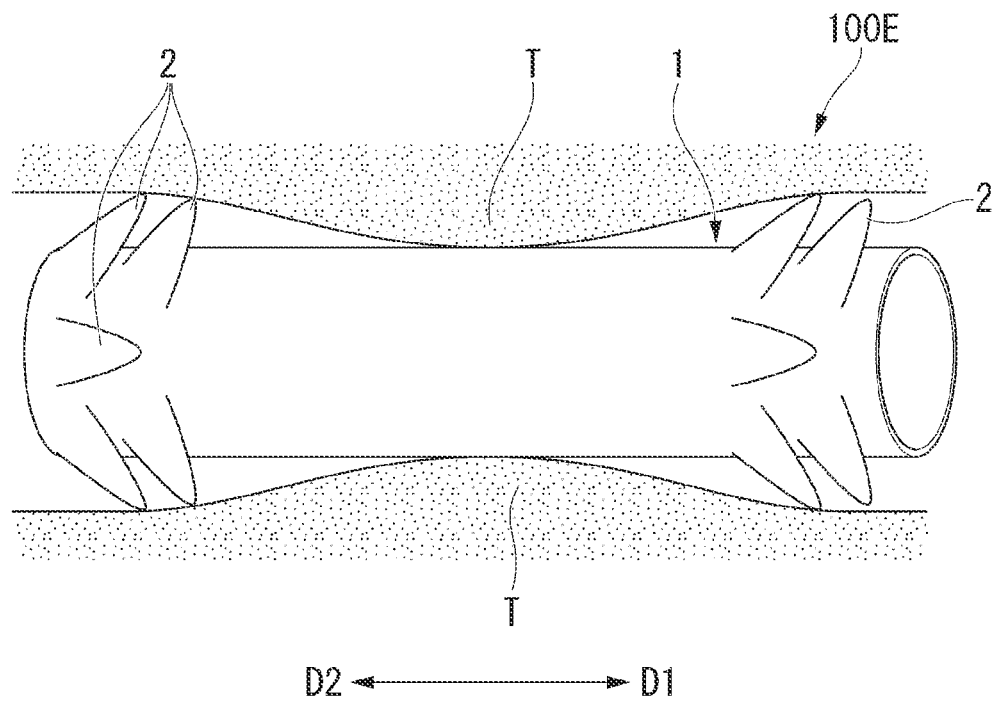
FIG. 10 is a view showing a modified example of the stent.

FIG. 10 is a view showing a stent 100E, which is a modified example of the stent 100. In the stent 100E, the locking parts 2 are provided on the side of the distal end part (the side of the first axial direction D1) of the stent 100E and the side of the proximal end part (the side of the second axial direction D2), and are not provided in an intermediate portion between the distal end part and the proximal end part. In a case in which a tumor T is present in the affected area in which stenosis or occlusion occurs, by disposing, an intermediate portion of the stent 100E in which the locking part 2 is not provided is disposed in the vicinity of the tumor T, thereby the tumor T is suitably prevented from being damaged by the stent.

Modified Example 3

Figure 11:
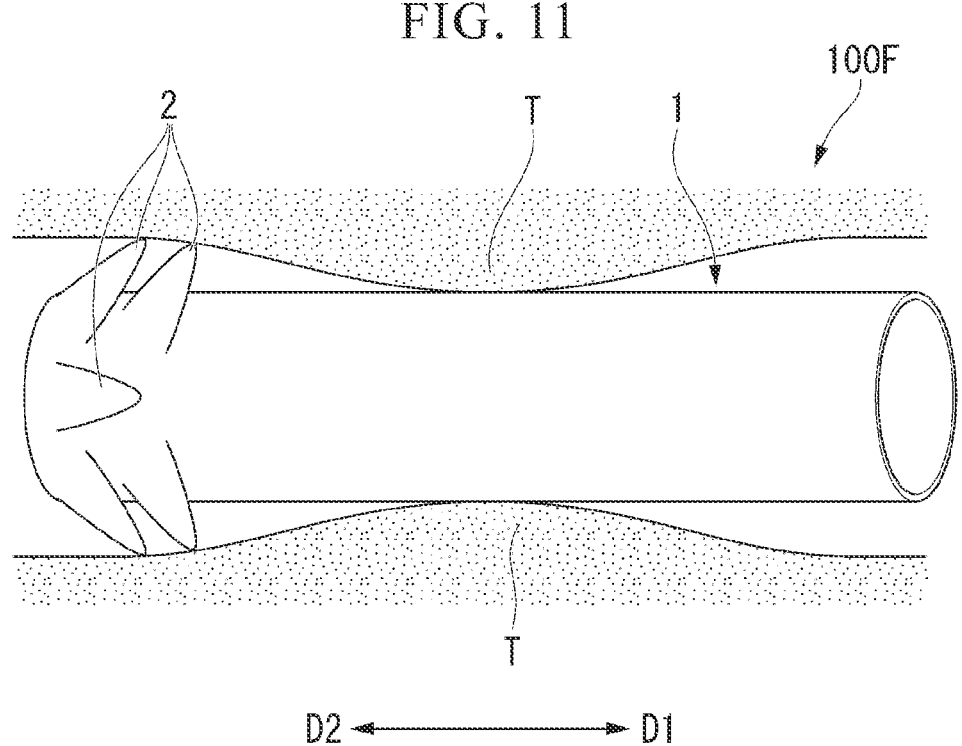
FIG. 11 is a view showing a modified example of the stent.

FIG. 11 is a view showing a stent 100F, which is a modified example of the stent 100. In the stent 100F, the locking part 2 is provided only on the side of the proximal end part (the side of the second axial direction D2) of the stent 100F, and is not provided on the side of the distal end part (the side of the first axial direction D1) and the intermediate portion between the distal end part and the proximal end part. Even in a case in which the released stent 100F is removed when the tumor T is present in the affected area in which stenosis or occlusion occurs, the tumor T is suitably prevented from being damaged by the stent.

Modified Example 4

Figure 12:
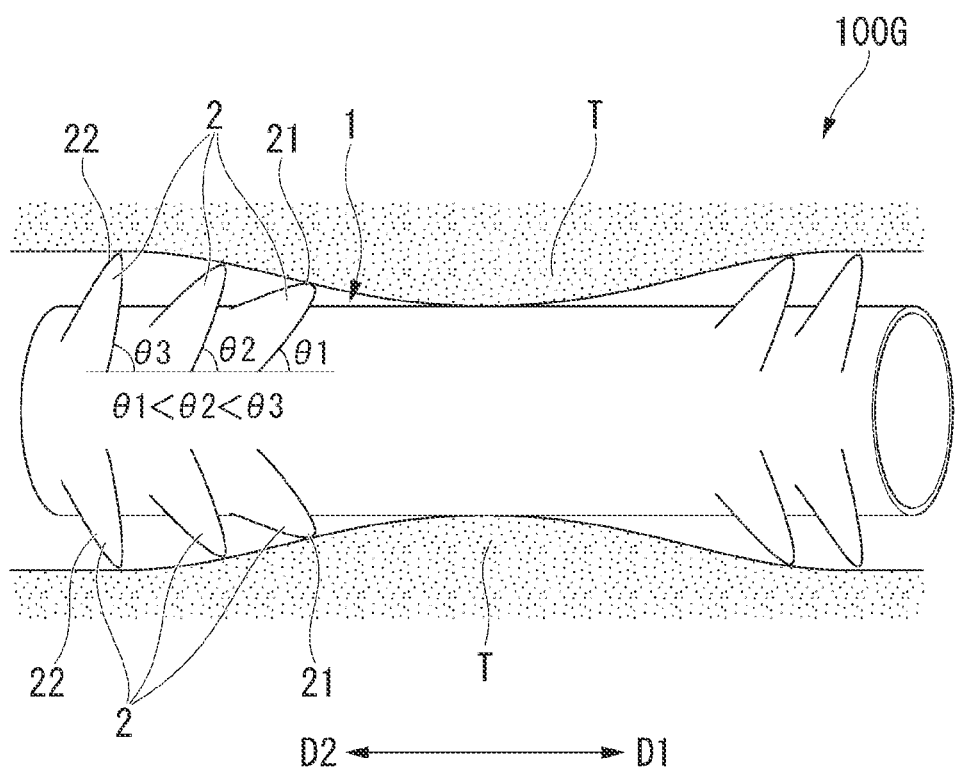
FIG. 12 is a view showing a modified example of the stent.

FIG. 12 is a view showing a stent 100G, which is a modified example of the stent 100. In the stent 100G, the angle formed by the protrusion direction of the locking part 2 and the axial direction of the body part 1 is different for each locking part 2. Among the plurality of the locking portions 2 of the stent 100G, first locking parts 21 are disposed at a center side of the body part, and second locking part 22 are disposed at the distal end part or the proximal end part of the body part 1. The first locking parts 21 are positioned at the center side of the body part 1 than the second locking part 22 in the axial direction. In the stent 100G, the angle formed by the protrusion direction of the locking part 2 and the axial direction of the body part 1 is greater as the locking part 2 is closer to the distal end part or the proximal end part. That is, the first angle of the first locking part 21 is greater than the second angle of the second locking part 22. In the stent 100G, the angle formed by the protrusion direction of the locking part 2 and the axial direction of the body part 1 is smaller as the locking part 2 is closer to the intermediate portion between the distal end part and the proximal end part. The stent 100G is capable of exerting the indwelling position maintenance function while suitably preventing the tumor T from damaging by the stent in a case in which the intermediate portion is disposed close to the tumor T.

EXAMPLE

Hereinafter, the present embodiment will be described in detail based on Example, but the technical scope of the present invention is not limited to Example.
Example 1 is the Stent 100 of the Embodiment Described Above.

Comparative Example 1 is a stent 200 in which all the non-entangled portions 6 of the stent 100 are replaced with the bent-crossing portions 5.

Expansion force measurement was carried out by using Example 1 and Comparative Example 1. The expansion force measurement was carried out based on "4 measurement of radial force" specified in JIS T3269. The stent disposed in a tank at 37° C. is alternately repeatedly reduced in diameter and expands in diameter with respect to the entire stent.

Figure 13:
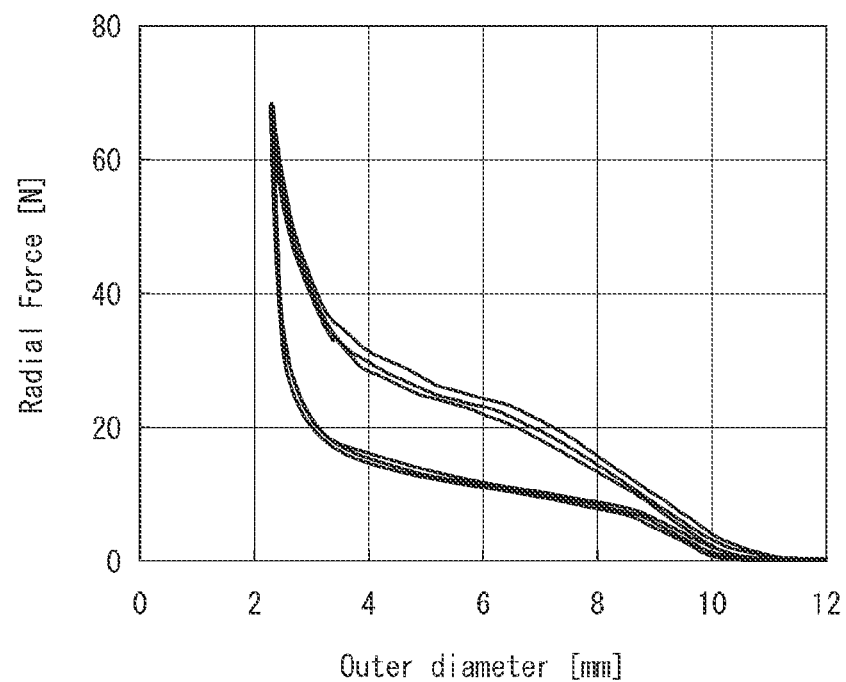
FIG. 13 is a graph showing a result of measurement of the expansion force of the stent in Example.
Figure 14:
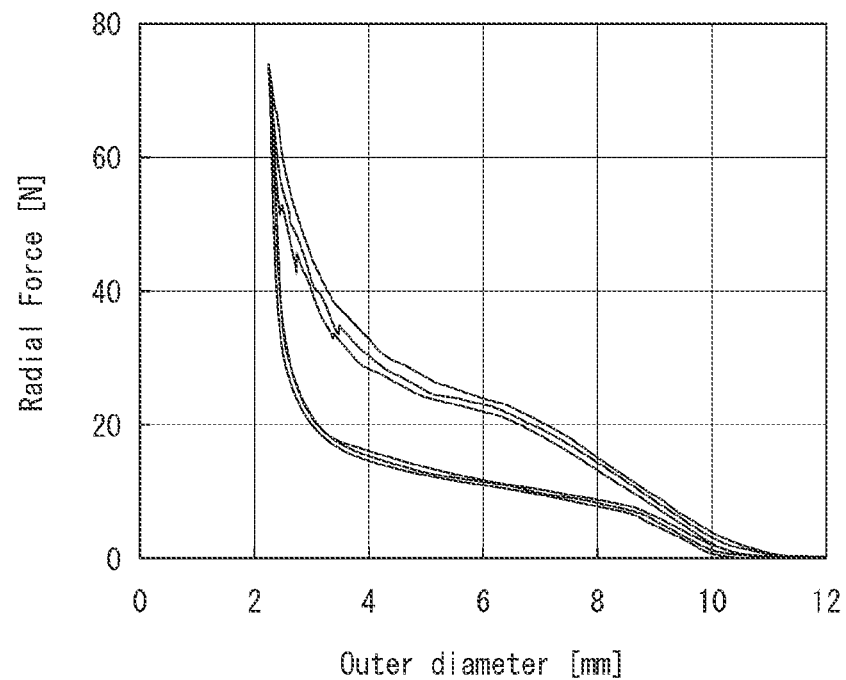
FIG. 14 is a graph showing a result of measurement of the expansion force of the stent in Comparative Example.

FIG. 13 shows a result of the expansion force measurement of the stent 100. FIG. 14 shows a result of the expansion force measurement of the stent 200. There is little difference in the expansion force of the stent between the stent 100 and the stent 200 when the diameter is reduced and when the diameter is expanded. That is, even in a case in which the locking part 2 is formed by replacing a part of the bent-crossing portion 5 with the non-entangled portion 6 as in the stent 100, the expansion force is hardly reduced, and a function of expanding stenosis or occlusion, which is a basic function of the stent, can be maintained.

The stent according to the present embodiment is capable of being applied to a medical device that expands the tubular portion of a human body from inside the lumen.

What is claimed is:

1. A stent having self-expandability, the stent comprising:
a body part formed in a tubular shape by a wire, the wire having a plurality of convex bent portions relative to a distal end of the body part and a plurality of concave bent portions relative to the distal end of the body part; and
the plurality of convex bent portions and the plurality of concave bent portions form a plurality of entangled portions and a plurality of locking parts;
wherein a first portion of the plurality of convex bent portions and a first portion of the plurality of concave bent portions cross each other, are entangled with each other and are movable relative to each other to form the plurality of entangled portions; and
a second portion of the plurality of convex bent portions and a second portion of the plurality of concave bent portions cross each other without being entangled, the second portion of the plurality of convex bent portions each extend radially outward from an outer circumferential surface of the body part to form the plurality of locking parts, the outer circumferential surface of the body part being defined by the wire other than the plurality of locking parts.

2. The stent according to claim 1, wherein
the plurality of locking parts comprises a first locking part and a second locking part; and
a first angle formed by a protrusion direction of the first locking part and an axial direction of the body part is different from a second angle formed by a protrusion direction of the second locking part and the axial direction.

3. The stent according to claim 2, wherein
the first locking part is disposed nearer a longitudinal center of the body part than the second locking part, and
the first angle is smaller than the second angle.

4. The stent according to claim 2, wherein the first angle is an acute angle.

5. The stent according to claim 1, wherein
the wire further having a plurality of first straight portions and a plurality of second straight portions to form a plurality of crossed portions; and
the plurality of first straight portions and the plurality of second straight portions cross each other without being entangled.

6. The stent according to claim 5, wherein the plurality of entangled portions, the plurality of crossed portions and the plurality of locking parts are disposed in a circumferential line extending circumferentially around the body part at a longitudinal position of the body part.

7. The stent according to claim 1, wherein the plurality of entangled portions and the plurality of locking parts are disposed in a circumferential line extending circumferentially around the body part at a longitudinal position of the body part.

8. The stent according to claim 1, wherein the second portion of the plurality of convex bent portions has a curved end.

9. The stent according to claim 1, wherein the second portion of the plurality of convex bent portions has a sharp end.

10. The stent according to claim 1, wherein the second portion of the plurality of convex bent portions has a plurality of curved ends.

11. The stent according to claim 1, wherein the plurality of locking parts are formed at only a distal end of the body part excluding a longitudinal center of the body part.

12. The stent according to claim 1, wherein the plurality of locking parts are formed at only a proximal end of the body part excluding a longitudinal center of the body part.

13. The stent according to claim 1, wherein the plurality of locking parts are formed at each of a distal end and a proximal end of the body part excluding a longitudinal center of the body part.

14. The stent according to claim 1, wherein the plurality of locking parts comprise a plurality of circumferential rows of locking parts, each row of the plurality of rows is formed at a different longitudinal position of the body part, an angle of the plurality of locking parts in each row of the plurality of circumferential rows of locking parts relative to the outer circumferential surface of body part increases as a longitudinal distance from a longitudinal center of the body part to each row of the plurality of circumferential rows of locking parts increases.

15. A method for indwelling a stent into a tubular organ, the stent including a body part formed in a tubular shape by a wire, the wire having a plurality of convex bent portions relative to a distal end of the body part and a plurality of concave bent portions relative to the distal end of the body part, the plurality of convex bent portions and the plurality of concave bent portions form a plurality of entangled portions and a plurality of locking parts, a first portion of the plurality of convex bent portions and a first portion of the plurality of concave bent portions cross each other, are entangled with each other and are movable relative to each other to form the plurality of entangled portions, and a second portion of the plurality of convex bent portions and a second portion of the plurality of concave bent portions cross each other without being entangled, the second portion of the plurality of convex bent portions each extend radially outward from an outer circumferential surface of the body part to form the plurality of locking parts, the outer circumferential surface of the body part being defined by the wire other than the plurality of locking parts, the method comprising:
    accommodating the stent being in a reduced diameter state into a delivery system;
    delivering the stent to an indwelling target position by the delivery system;
    indwelling the stent while expanding a diameter of the stent into the tubular organ by the delivery system such that the plurality of locking parts hold the stent at the indwelling target position.

16. The method according to claim 15, wherein
    the plurality of locking parts comprises a first locking part and a second locking part; and
    a first angle formed by a protrusion direction of the first locking part and an axial direction of the body part is different from a second angle formed by a protrusion direction of the second locking part and the axial direction.

17. The method according to claim 16, wherein
    the first locking part is positioned nearer a longitudinal center of the body part than the second locking part, and
    when indwelling the stent into the tubular organ, the stent is indwelled while expanding a diameter of the stent by the delivery system such that the first angle is smaller than the second angle.

18. The method according to claim 16, wherein the first angle is an acute angle.

19. A stent having self-expandability, the stent comprising:
    a body part formed in a tubular shape by a wire, the wire having a plurality of convex bent portions relative to a distal end of the body part and a plurality of concave bent portions relative to the distal end of the body part; and
    the plurality of convex bent portions and the plurality of concave bent portions form a plurality of entangled portions and a plurality of locking parts;
    wherein a first portion of the plurality of convex bent portions and a first portion of the plurality of concave bent portions cross each other, are entangled with each other and are movable relative to each other to form the plurality of entangled portions;
    a second portion of the plurality of convex bent portions and a second portion of the plurality of concave bent portions cross each other without being entangled, the second portion of the plurality of convex bent portions extends radially outward from an outer circumferential surface of the body part to form the plurality of locking parts, the outer circumferential surface of the body part being defined by the wire other than the plurality of locking parts; and
    the plurality of locking parts are each formed at a different longitudinal position of the body part, an angle of the plurality of locking parts relative to the outer circumferential surface of the body part only increases as a longitudinal distance from a longitudinal center of the body part to each of the plurality of locking parts increases.

20. The stent according to claim 19, wherein the plurality of locking parts are arranged in a plurality of circumferential rows of locking parts each formed at a different longitudinal position of the body part, the angle of the plurality of locking parts in each of the plurality of circumferential rows of locking parts relative to the outer circumferential surface of body part only increases as the longitudinal distance from the longitudinal center of the body part to each of the plurality of circumferential rows of locking parts increases.

* * * * *